US007728063B2

(12) United States Patent
Brodt et al.

(10) Patent No.: US 7,728,063 B2
(45) Date of Patent: Jun. 1, 2010

(54) COPOLYMERS COMPRISING N-HETEROCYCLIC GROUPS, AND USE THEREOF AS AN ADDITIVE IN DETERGENTS

(75) Inventors: Gregor Brodt, Heppenheim (DE); Pia Baum, Weinheim (DE); Tanja Seebeck, Bensheim (DE); Marcus Guzmann, Muehlhausen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 633 days.

(21) Appl. No.: 11/587,584

(22) PCT Filed: Apr. 26, 2005

(86) PCT No.: PCT/EP2005/004467

§ 371 (c)(1), (2), (4) Date: Oct. 25, 2006

(87) PCT Pub. No.: WO2005/105968

PCT Pub. Date: Nov. 10, 2005

(65) Prior Publication Data

US 2007/0244023 A1 Oct. 18, 2007

(30) Foreign Application Priority Data

Apr. 27, 2004 (DE) ...................... 10 2004 020 544

(51) Int. Cl.

| | |
|---|---|
| ***A61K 9/16*** | (2006.01) |
| ***C08F 8/30*** | (2006.01) |
| ***C08F 290/06*** | (2006.01) |
| ***C08F 20/58*** | (2006.01) |
| ***C08F 18/00*** | (2006.01) |
| ***C08F 16/12*** | (2006.01) |
| ***C08F 116/12*** | (2006.01) |

(52) U.S. Cl. ...................... 524/543; 524/555; 524/558; 526/304; 526/320; 526/332; 526/333

(58) Field of Classification Search ................. 526/304, 526/320, 332, 333; 524/543, 555, 558
See application file for complete search history.

(56) References Cited

U.S. PATENT DOCUMENTS

| | | | | |
|---|---|---|---|---|
| 4,892,916 | A * | 1/1990 | Hawe et al. ................. | 526/304 |
| 6,172,027 | B1 | 1/2001 | Boeckh et al. | |
| 2004/0030206 | A1 * | 2/2004 | Dahlmann et al. ............ | 585/15 |

FOREIGN PATENT DOCUMENTS

| | | |
|---|---|---|
| DE | 42 35 798 | 4/1994 |
| DE | 196 21 509 | 12/1997 |
| DE | 19805232 | 8/1999 |
| DE | 101 56 133 | 5/2003 |
| DE | 101 56 134 | 5/2003 |
| WO | 98 30664 | 7/1998 |
| WO | 03 042262 | 5/2003 |
| WO | 2004050730 | 6/2004 |

* cited by examiner

*Primary Examiner*—William K Cheung
(74) *Attorney, Agent, or Firm*—Oblon, Spivak, McClelland, Maier & Neustadt, L.L.P.

(57) ABSTRACT

The present invention relates to the use of a copolymer comprising, in polymerized form, (a) from 80 to 99.9 mol %, based on the total amount of the monomers polymerized to prepare the copolymer, of at least one monomer A which in each case comprises a heterocycle having at least 1 nitrogen atom and composed of from 3 to 10 ring members and a $C_2$-$C_6$-alkenyl group bonded to a carbon or nitrogen ring atom of the heterocycle; and (b) from 0.1 to 20 mol %, based on the total amount of the monomers polymerized to prepare the copolymer, of at least one monomer B copolymerizable with monomer A, said monomer B having a monoethylenically unsaturated double bond and also a linear or branched poly-$C_2$-$C_4$-alkylene oxide group having on average from 4 to 500 $C_2$-$C_4$-alkylene oxide units, in liquid and in solid detergent formulations. In addition, the invention relates to a process for preparing such a copolymer, and also to a liquid or solid detergent formulation comprising at least one such copolymer.

14 Claims, No Drawings

COPOLYMERS COMPRISING N-HETEROCYCLIC GROUPS, AND USE THEREOF AS AN ADDITIVE IN DETERGENTS

The present invention relates to novel copolymers having N-heterocyclic groups and to their use in liquid and solid detergent formulations. In the wash process, these copolymers exhibit dye transfer-inhibiting action.

During the washing operation, dye molecules are often detached from colored textiles and can in turn attach to other textiles. In order to counteract this undesired dye transfer, dye transfer inhibitors are often used. These are frequently polymers which contain monomers having nitrogen heterocycle radicals (=N-heterocyclic groups or N-heterocycles) in copolymerized form.

For example, DE 4235798 describes copolymers of a) 1-vinylpyrrolidone, 1-vinylimidazole, 1-vinylimidazolium compounds or mixtures thereof; b) further nitrogen-containing, basic ethylenically unsaturated monomers; and if appropriate c) other monoethylenically unsaturated monomers, and their use to inhibit dye transfer during the washing operation.

For this purpose, similar copolymers are described in DE 19621509 and WO 98/30664.

Some of the copolymers described in these documents feature good inhibition of dye transfer in washing processes. However, they generally have low compatibility with the further detergent constituents typically used. For instance, especially in the case of liquid detergents, there is the risk of incompatibilities, for example in the form of cloudiness or phase separations.

To solve the problem of compatibility, DE 10156134 proposes, as dye transfer inhibitors, graft polymers which contain A) a polymeric graft base without monoethylenically unsaturated units and B) polymeric side chains formed by polymerizing a cyclic, 3- to 7-membered N-vinylamide, the proportion of side chains (B) in the overall polymer being $\geqq$60% by weight. Similar graft polymers are described for this purpose in DE 10156135 and DE 10156133.

Although such graft polymers feature improved compatibility with detergent constituents, especially of liquid detergents, the disadvantage of poorer dye transfer inhibition at the same time has to be accepted for this advantage. In addition, the compatibility achieved is not fully satisfactory.

The prior German patent application 10256162.2 discloses copolymers of vinyllactams with (meth)acrylic esters of alkyl polyalkylene glycols which, on the end groups of the polyether chain, have an aliphatic hydrocarbon radical having from 3 to 40 carbon atoms.

It is therefore an object of the present invention to provide polymers having good dye transfer-inhibiting action in the course of the washing operation and have good compatibility with conventional detergent constituents, especially in the case of liquid formulations.

It has been found that, surprisingly, this object is achieved by copolymers based on monomers having N-heterocycles (monomers A) which contain ethylenically unsaturated monomers B having polyalkylene oxide groups in an amount of from 0.1 to 20 mol % in copolymerized form.

Accordingly, the present invention relates to the use of such copolymers in liquid or solid detergent formulations, comprising in polymerized form:

(a) from 80 to 99.9 mol % of at least one monomer A which in each case comprises a heterocycle having at least 1 nitrogen atom (N-heterocycle) and composed of from 3 to 10 ring members and a $C_2$-$C_6$-alkenyl group bonded to a carbon or nitrogen ring atom of the heterocycle; and (b) from 0.1 to 20 mol % of at least one monomer B copolymerizable with monomer A, said monomer B including a monoethylenically unsaturated double bond and also a linear or branched poly-$C_2$-$C_4$-alkylene oxide group having on average from 4 to 500 $C_2$-$C_4$-alkylene oxide units and 1 or 2 terminal radicals selected independently from $C_1$-$C_2$-alkyl, all quantitative data on monomers in mol % here and hereinbelow being based on the total amount of monomers used to prepare the copolymers.

The invention also relates to such copolymers, with the proviso that the end group of the poly-$C_2$-$C_4$-alkylene oxide group in the monomers B is selected from $C_1$-$C_2$-alkyl when monomer B is an ester of an ethylenically unsaturated carboxylic acid with a linear poly-$C_2$-$C_4$-alkylene oxide. The invention further relates to a process for preparing such copolymers comprising the free-radical polymerization of at least one monomer A with the at least one monomer B.

Here and hereinbelow, N-heterocycle represents an aromatic or nonaromatic, heterocyclic radical having generally from 3 to 10, in particular from 4 to 8 and especially from 5 to 7 ring atoms, and 1, 2 or 3 of the ring atoms are heteroatoms which are preferably selected from nitrogen and oxygen, and at least 1 ring member is a nitrogen atom. The N-heterocycle may be aromatic (heteroaryl) or partially or fully saturated. In addition, the N-heterocycle may optionally have one or more, for example 1, 2, 3 or 4, substituents selected from $C_1$-$C_4$-alkyl, $C_3$-$C_6$-cycloalkyl and phenyl. In addition, the N-heterocycle may have a carbonyl group and/or an N-oxide group as a ring member. Otherwise, the N-heterocycle may be present in quaternized form, for example by alkylation of at least one ring nitrogen atom. Moreover, the N-heterocycle may also be present as a betainic structure, in which at least one nitrogen atom of the heterocycle is bonded via a $C_1$-$C_{20}$-alkanediyl group to an anionic group selected from —$SO_3^-$, —$OSO_3^-$, —$COO^-$, —$OPO(OH)O^-$, —$OPO(OR^f)O^-$ or —$PO(OH)O^-$, where $R^f$ is $C_1$-$C_6$-alkyl. Here, $C_1$-$C_{20}$-alkanediyl means a linear or branched, aliphatic, divalent hydrocarbon radical, i.e. bonded via two carbon atoms, and generally having from 1 to 20 and in particular from 1 to 10, carbon atoms.

Here and hereinbelow, alkyl represents a linear or branched, aliphatic hydrocarbon radical having generally from 1 to 10, in particular from 1 to 6 and especially from 1 to 4 carbon atoms, for example methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl, 1-ethyl-3-methylpropyl, n-heptyl, n-octyl, n-nonyl, n-decyl, 1-methylhexyl, 1-ethylhexyl, 2-ethylhexyl, 1-methylheptyl, 1-methyloctyl or 1-methylnonyl.

Here and hereinbelow, cycloalkyl represents a cycloaliphatic hydrocarbon radical having generally from 3 to 6 carbon atoms, for example cyclopropyl, cyclobutyl, cyclopentyl or cyclohexyl.

Here and hereinbelow, alkenyl represents a monoethylenically unsaturated hydrocarbon radical having generally from 2 to 6 and in particular from 2 to 3 carbon atoms, for example vinyl, propen-1-yl, propen-2-yl, allyl, 1-buten-1-yl, 1-buten- 2-yl, 2-methylpropen-3-yl(methallyl), 1-penten-2-yl and 1-hexen-2-yl. In particular, alkenyl represents vinyl and allyl, more preferably allyl.

$C_2$-$C_4$-Alkylene oxide represents a linear or branched alkanediyloxy group having generally from 2 to 4 and in particular 2 carbon atoms, such as $CH_2CH_2O$, $(CH_2)_3O$, $(CH_2)_4O$, $CH(CH_3)—CH_2O$, $CH_2—CH(CH_3)O$, $CH_2—C(CH_3)_2O$, $CH(CH_3)—CH(CH_3)—O$, $C(CH_3)_2—CH_2O$, $CH_2CH(CH_3)—CH_2O$, $CH(CH_3)—(CH_2)_2O$ and $(CH_2)_2—CH(CH_3)O$, in particular one of the aforementioned alkane-1,2-diyloxy groups and especially $CH_2CH_2O$.

The monomers A include cyclic lactams which bear, on their nitrogen atom, a $C_2$-$C_6$-alkenyl radical, in particular a vinyl radical. Such lactams may be described by the general formula (III)

(III)

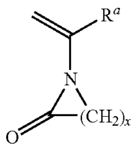

where x is an integer in the range from 1 to 6; and $R^a$ is H or $C_1$-$C_4$-alkyl;

and where one or more of the $CH_2$ groups forming the lactam ring optionally have 1 or 2 substituents selected from $C_1$-$C_4$-alkyl. The N-vinyllactams preferred among the lactams III have in particular from 5 to 7 ring atoms. Examples of such N-vinyllactams are N-vinylpyrrolidones, for example N-vinyl-3-methylpyrrolidone and N-vinylpyrrolidone; N-vinylcapro- and -valerolactams, for example N-vinyl-3-methyl-ε-caprolactam, N-vinyl-ε-caprolactam and N-vinyl-δ-valerolactam; N-vinylpiperidone and N-vinyloxazolidones, for example N-vinyl-5-methyloxazolidone and N-vinyloxazolidone. Preferred N-vinyllactams are N-vinylpyrrolidone, N-vinyl-ε-caprolactam and N-vinyl-δ-valerolactam, more preferably N-vinylpyrrolidone. The lactams III are also referred to hereinbelow as monomers A1.

The monomers A also include N-vinylheterocyclic monomers having an N-heterocycle selected from imidazoles, imidazolines and imidazolidines, pyridines, pyrroles, pyrrolidines, quinolines, isoquinolines, purines, pyrazoles, triazoles, tetraazoles, indolizines, pyridazines, pyrimidines, pyrazines, indoles, isoindoles, oxazoles, oxazolidines, morpholines, piperazines, piperidines, isoxazoles, thiazoles, isothiazoles, indoxyls, isatins, dioxindoles and hydantoins and also derivatives thereof, for example barbituric acid, uracil and derivatives thereof. The monomers A other than the lactams III are also referred to hereinbelow as monomers A2. The monomers A2 mentioned may also be used in the form of betainic derivatives or quaternized products.

N-Heterocycles used in the monomers A2 are in particular selected from imidazoles, pyridines, pyridine N-oxides and betainic derivatives and quaternization products thereof, especially from imidazoles.

In a preferred embodiment, the monomers A2 are selected from N-vinylimidazoles of the general formula IV a, betainic N-vinylimidazoles of the general formula IV b, 2- and 4-vinylpyridines of the general formulae IV c and IV d, and betainic 2- and 4-vinylpyridines of the general formulae IV e and IV f:

IV a

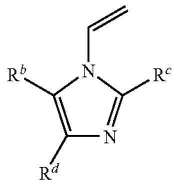

IV b

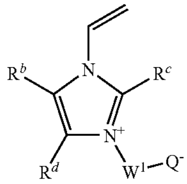

IV c

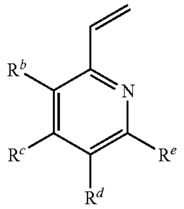

IV d

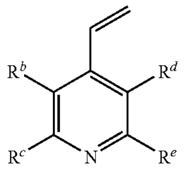

IV e

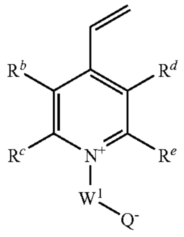

IV f

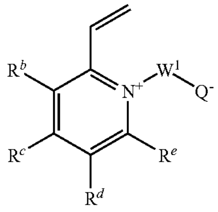

where $R^b$, $R^c$, $R^d$, $R^e$ are each independently H, $C_1$-$C_4$-alkyl or phenyl, preferably H or $C_1$-$C_4$-alkyl, more preferably H;

$W^1$ is $C_1$-$C_{20}$-alkylene, for example $—CH_2—$, $—CH(CH_3)—$, $—(CH_2)_2—$, $—CH_2—CH(CH_3)—$, $—(CH_2)_3—$, $—(CH_2)_4—$, $—(CH_2)_5—$, $—(CH_2)_6—$, preferably $C_1$-$C_3$-alkylene; in particular $—CH_2—$, $—(CH_2)_2—$ or $—(CH_2)_3—$;

$Q^-$ is $—SO_3^-$, $—OSO_3^-$, $—COO^-$, $—OPO(OH)O^-$, $—OPO(OR^f)O^-$ or $—PO(OH)O^-$; and $R^f$ is $C_1$-$C_{24}$-alkyl such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, n-octyl, n-nonyl, n-decyl; more preferably $C_1$-$C_4$-alkyl.

Particularly preferred monomers A2 are N-vinylimidazole and $C_1$-$C_4$-alkylvinylimidazoles, for example N-vinyl-2-methylimidazole, N-vinyl-4-methylimidazole, N-vinyl-5-methylimidazole, N-vinyl-2-ethylimidazole, in particular N-vinylimidazole and methylvinylimidazoles, especially N-vinylimidazole and N-vinyl-2-methylimidazole; 3-vinylimidazole N-oxide; 2- and 4-vinylpyridines, for example 2-vinyl-4-methylpyridine, 2-vinyl-6-methylpyridine and 2- and 4-vinylpyridine; vinylpyridine N-oxides such as 2- and 4-vinylpyridine N-oxide, for example 2-vinyl-4-methylpyridine N-oxide, 4-vinyl-2-methylpyridine N-oxide and 2- and 4-vinylpyridine N-oxide; and also betainic derivatives and quaternization products thereof.

Particularly preferred betainic monomers A2 are monomers of the formulae IV b, IV e and IV f in which the $W^1$—$X^-$ moiety represents —$CH_2$—$COO^-$, —$(CH_2)_2$—$SO_3^-$ or —$(CH_2)_3$—$SO_3^-$, and $R^b$, $R^c$, $R^d$, $R^e$ each represent H.

The quaternized monomers A2 used are preferably vinylimidazoles and vinylpyridines, these having been quaternized before or after the polymerization. Particular preference is given to using 1-methyl-3-vinylimidazolium methosulfate and methochloride.

The quaternization may in particular be undertaken using alkylating agents such as alkyl halides which generally have from 1 to 24 carbon atoms in the alkyl radical, or dialkyl sulfates which generally contain alkyl radicals having from 1 to 10 carbon atoms. Examples of suitable alkylating agents from these groups are methyl chloride, methyl bromide, methyl iodide, ethyl chloride, ethyl bromide, propyl chloride, hexyl chloride, dodecyl chloride, lauryl chloride, and also dimethyl sulfate and diethyl sulfate. Further suitable alkylating agents are, for example, benzyl halides in particular benzyl chloride and benzyl bromide; chloroacetic acids; methyl fluorosulfate; diazomethane; oxonium compounds such as trimethyloxonium tetrafluoroborate; alkylene oxides such as ethylene oxide, propylene oxide and glycidol which are used in the presence of acids; cationic epichlorohydrins. Preferred quaternizing agents are methyl chloride, dimethyl sulfate and diethyl sulfate.

Also useful as monomers A are mixtures of the aforementioned monomers A1 and A2.

In a preferred embodiment, at least 85 mol % and especially 90 mol % of the monomers A are selected from the monomers A1 (N-vinyllactams) and more preferably from N-vinylpyrrolidones. A very particularly preferred N-vinyllactam is N-vinylpyrrolidone. Particular preference is given to the N-vinyllactams and in particular N-vinylpyrrolidone being the sole monomer A.

In a further preferred embodiment, the monomers A comprise at least one N-vinyllactam as monomer A1 and at least one different monomer A2, in particular an N-vinylimidazole. The molar A1:A2 ratio is then preferably in the range from 9:1 to 1:9, in particular from 4:1 to 1:4.

In a particularly preferred embodiment, the monomers A are selected from N-vinylpyrrolidone and mixtures of N-vinylpyrrolidone with N-vinylimidazole.

For the dye transfer-inhibiting action of the inventive copolymers, it has been found to be advantageous when the proportion of the monomers A amounts to at least 85 mol % and in particular at least 90 mol %, of the total amount of the monomers used to prepare the copolymers. In particular, the proportion of the monomers A, based on the total amount of monomers, is from 85 mol % to 99.5 mol % and more preferably from 90 to 99 mol %.

It has also been found to be advantageous for the inventive purposes when the proportion of ethylene oxide units in the poly-$C_2$-$C_4$-alkylene oxide group of the monomers B is selected such that it is at least 50 mol %, in particular 75 mol % and especially about 100 mol %, based on the $C_2$-$C_4$-alkylene oxide units present in monomer B.

By its nature, the poly-$C_2$-$C_4$-alkylene oxide group of the monomers B has 2 end groups in the case of a linear structure and 3 or more end groups in the case of a branched structure, of which one bears an ethylenically unsaturated group. The remaining terminal radicals (end groups) may be hydrogen or OH or an organic radical. Preferred organic end groups have from 1 to 10 carbon atoms in particular from 1 to 4 carbon atoms and are typically selected from H, $C_1$-$C_{10}$-alkyl and benzyl (or OH, $C_1$-$C_{10}$-alkyloxy and benzyloxy), in particular from H and $C_1$-$C_4$-alkyl and especially from $C_1$-$C_2$-alkyl. The monomers B preferably have 1 or 2 such end groups and in particular 1 end group.

Monomers B suitable in accordance with the invention preferably have the general formula (I):

$$X—CH{=}CR^1—Y—Z \qquad (I)$$

where

X is H or COOH;

$R^1$ is $C_1$-$C_4$-alkyl such as methyl, ethyl, n-propyl, isopropyl, n-butyl, isobutyl, sec-butyl and tert-butyl, in particular H or methyl;

Y is O, $CH_2$—O, C(O)O, C(O)NH, NHC(O) or $CH_2$—NHC(O); and

Z is a linear or branched poly-$C_2$-$C_4$-alkylene oxide group comprising on average from 4 to 500 $C_2$-$C_4$-alkylene oxide units and 1 or 2 terminal radicals each independently selected from H, $C_1$-$C_{10}$-alkyl and benzyl, preferably from H and $C_1$-$C_4$-alkyl and especially from $C_1$-$C_2$-alkyl.

When the orientation of the Y radicals on incorporation into the formula (I) can be realized in different ways, the incorporation, in the manner specified above, is read from left to right.

In the specification of the number of $C_2$-$C_4$-alkylene oxide units in the linear or branched poly-$C_2$-$C_4$-alkylene oxide group Z, the expression "on average" refers here and hereinbelow to the numerical average of the alkylene oxide units per monomer B. The term degree of alkoxylation is also used synonymously.

The linear or branched poly-$C_2$-$C_4$-alkylene oxide groups Z generally have a degree of alkoxylation in the range from 4 to 500, in particular from 6 to 200 and especially from 6 to 100.

The poly-$C_2$-$C_4$-alkylene oxide groups Z of the monomers B preferably have a linear or branched structure of the formulae (II.1) or (II.2):

$$—Z^1—O—[Z^2—O]_n—R^2 \qquad (II.1)$$

or $$—Z^4(—O—[Z^2—O]_m—R^2)(—O—[Z^3—O]_k—R^3) \qquad (II.2)$$

where $Z^1$, $Z^2$ and $Z^3$ are each independently $C_2$-$C_4$-alkanediyl;

$Z^4$ is $C_2$-$C_4$-alkanetriyl;

n+1 and m+k+1 are each an integer and the average of n+1 and m+k+1 is each in the range from 4 to 500, in particular from 6 to 200 and especially from 6 to 100; and $R^2$ and $R^3$ are each independently H, $C_1$-$C_{10}$-alkyl or benzyl, preferably H or $C_1$-$C_4$-alkyl and especially $C_1$-$C_2$-alkyl.

Here and hereinbelow, alkanetriyl represents a linear or branched aliphatic, trivalent hydrocarbon radical preferably bonded via three different carbon atoms and having generally from 2 to 4, in particular 3 carbon atoms.

In the formulae (II.1) and (II.2), the $Z^2$ or $Z^2$ and $Z^3$ radicals are preferably each at least 50%, more preferably at least 75% and most preferably about 100% ethylene oxide units.

In a preferred embodiment, the $R^2$ and $R^3$ radicals in the formulae (II.1) and (II.2) are each independently methyl.

Preference is given in particular to monomers B of the formula (I) in which Z is a radical of the formula (II.1).

In a further preferred embodiment, in formula (I), the variable X is H and Y is C(O)O or C(O)NH. In this embodiment, in formula (I), the variable Z has in particular one of the abovementioned preferred structures of the formulae (II.1) or (II.2). $R^1$ is in particular hydrogen or methyl. Particular preference is given to the methyl poly-$C_2$-$C_3$-alkylene glycol esters of acrylic acid or of methacrylic acid, and among these in particular to those having a proportion of at least 50 mol %, in particular of at least 80 mol % of ethylene oxide groups, based in each case on the total amount of $C_2$-$C_3$-alkylene oxide groups, and especially to the methyl polyethylene glycol esters of (meth)acrylic acid.

In a further preferred embodiment, in formula (I), the variable X is H and Y is $CH_2$—O. In this embodiment, in formula (I), the variable Z has in particular one of the abovementioned preferred structures of the formulae (II.1) or (II.2). $R^1$ is in particular hydrogen or methyl. Particular preference is given to the allyl ether $C_2$-$C_3$-alkoxylates ($R^1$=H) and 2-methyl allyl $C_2$-$C_3$-alkoxylate ($R^1$=methyl), in particular to those having a terminal methyl group, and among these especially to those having a proportion of at least 50 mol %, in particular of at least 80 mol % of ethylene oxide groups, based in each case on the total amount of $C_2$-$C_3$-alkylene oxide groups, and very especially to the allyl ether ethoxylates ($R^1$=H).

The monomers B may be prepared by standard organic chemistry processes which are known to those skilled in the art (see, for example, Houben-Weyl, Methoden der organischen Chemie, Georg-Thieme-Verlag, Stuttgart, 1954), for example by esterification, amidation, transamidation, transesterification or alkoxylation of suitable (meth)acrylic acids, (meth)acrylic esters, (meth)acrylamides, and also maleic acid, maleic (mono)esters, maleic (mono)amides; by alkoxylation of allyl alcohol; by etherification of allyl halides with poly-$C_2$-$C_4$-alkylene oxides and vinylation of polyalkylene oxides having OH or NH terminus with acetylene. Accordingly, for example, methyl polyethylene glycol (meth)acrylic acid may in particular be obtained by esterifying (meth) acrylic acid with polyethylene glycol monomethyl ethers.

Allyl alcohol polyalkoxylates suitable as monomers B are also commercially available, for example under the name Pluriol® A 010 R and Pluriol® A 11 RE from BASF Aktiengesellschaft.

With regard to the dye transfer-inhibiting performance of the inventive copolymers in typically used detergents, it has been found to be advantageous when the proportion of monomers B accounts for at most 15 mol % and in particular at most 10 mol %, of the total amount of the monomers used to prepare the copolymers. In particular, the proportion of monomers B is from 0.5 to 15 mol % and more preferably from 1 to 10 mol %.

In addition to monomers A and B, the inventive copolymers may also contain one or more further monomers C copolymerizable with monomers A and B. Examples of monomers C are monoethylenically unsaturated $C_3$-$C_{10}$-mono- and $C_4$-$C_{10}$-dicarboxylic acids, for example (meth)acrylic acid, crotonic acid, fumaric acid and maleic acid; ethylenically unsaturated sulfonic acids and salts thereof, such as vinylsulfonic acid, 2-acryloyloxyethanesulfonic acid, 2- and 3-acryloyloxypropanesulfonic acid, 2-methyl-2-acrylamidopropanesulfonic acid and styrenesulfonic acid and also sodium salts thereof; vinyl esters of saturated $C_1$-$C_{10}$-carboxylic acids, for example vinyl acetate and vinyl propionate; vinyl and allyl ethers of linear or branched $C_1$-$C_{10}$-alcohols, for example vinyl ethyl ether, vinyl propyl ether, allyl methyl ether, allyl ethyl ether and allyl propyl ether; vinylformamides, for example N-vinyl-N-methylformamide and N-vinylformamide itself; the quaternary products of N-vinyl- and N-allylamines, such as alkylated N-vinyl and N-allylamines, for example N-vinylmethylamine, N-vinylethylamine, N-allylmethylamine, N-allylethylamine and N-allylpropylamine; the esters of monoethylenically unsaturated $C_3$-$C_6$-monocarboxylic acids or $C_4$-$C_6$-dicarboxylic acids with linear or branched aliphatic $C_1$-$C_{10}$-alcohols, for example methyl acrylate, ethyl acrylate, methyl methacrylate, ethyl methacrylate, dimethyl maleate, diethyl maleate, 2-ethylhexyl acrylate and 2-ethylhexyl methacrylate; the monoesters of monoethylenically unsaturated $C_4$-$C_6$-dicarboxylic acids with linear or branched $C_1$-$C_{10}$-alcohols, for example monomethyl maleate or monoethyl maleate; the anhydrides of monoethylenically unsaturated $C_4$-$C_6$-dicarboxylic acids, for example maleic anhydride; amides of monoethylenically unsaturated $C_3$-$C_6$-carboxylic acids with primary and secondary $C_1$-$C_{12}$-amines, for example (meth)acrylamide, N-methyl(meth) acrylamide, N-isopropyl(meth)-acrylamide or N-butyl(meth) acrylamide; unsaturated nitriles, for example acrylonitrile and methacrylonitrile; and the salts of the acids mentioned, the derivatives thereof and also mixtures thereof.

The demands of certain applications may influence the selection of the type and amount of the monomers C. For instance, it may be desirable to further convert the inventive polymers in a selective manner before use, for example by selective alcoholysis, aminolysis or hydrolysis. For instance, units corresponding to vinyl alcohol units may in particular be formed from vinyl ester building blocks and units corresponding to vinylamine units from vinylformamide units.

In a preferred embodiment, the monomer C is selected from monoethylenically unsaturated $C_3$-$C_{10}$-mono- and $C_4$-$C_{10}$-dicarboxylic acids, in particular acrylic acid, methacrylic acid and maleic acid.

In a preferred embodiment, the proportion of monomers C is less than 20 mol %, in particular less than 15 mol % and especially less than 10 mol %, based on the total weight of the copolymer.

In further embodiment, the proportion of the monomers C is from 1 to 20 mol %, in particular from 1 to 15 mol %, based on the total weight of the copolymer.

The K values of the copolymers used in accordance with the invention are typically from 10 to 150, preferably from 10 to 80 and more preferably from 15 to 60 (determined according to H. Fikentscher, Cellulose-Chemie, Vol. 13, p. 58 to 64 and 71 to 74 (1932) in water or aqueous sodium chloride solutions at 25° C. (NaCl concentration from 0.1 to 7.0% by weight) and polymer concentrations which, depending on the K value range, are from 0.1% by weight to 5% by weight). The K value desired in each case can be set by the composition of the starting materials.

The present invention further relates to a process for preparing the inventive copolymers, in which the at least one monomer A is free-radically polymerized with the at least one monomer B and, if appropriate, with the monomers C.

The free-radical polymerization of the monomers may be carried out by all known methods such as solution polymerization, emulsion polymerization, suspension polymerization or bulk polymerization; preference is given to the processes of solution polymerization and of bulk polymerization, very particular preference to solution polymerization.

Advantageously, a solution polymerization is carried out in water or in mixtures of water with organic solvents as the reaction medium. However, it is also possible to use organic solvent (mixtures) alone as the reaction medium.

Examples of suitable organic solvents are aliphatic and cycloaliphatic monohydric $C_1$-$C_4$-alcohols, for example methanol, ethanol, n-propanol, isopropanol, n-butanol, sec-butanol and tert-butanol; polyhydric alcohols such as $C_1$-$C_4$-glycols, for example ethylene glycol, propylene glycol and butylene glycol and glycerol; mono- and dialkyl ethers of polyhydric alcohols such as $C_1$-$C_4$-alkyl ethers of the polyhydric alcohols mentioned, for example monomethyl ethylene glycol, monoethyl ethylene glycol, dimethyl ethylene glycol and dimethyl propylene glycol; ether alcohols, for example diethylene glycol and triethylene glycol; and also cyclic ethers, for example dioxane. Preferred organic solvents are alcohols.

Preference is given to carrying out the polymerization in an aqueous polymerization medium which contains at least 50% by volume, in particular at least 80% by volume and more preferably at least 95% by volume, of water, based on the total amount of solvent. Particular preference is given to carrying out the polymerization in water.

When solution polymerization is carried out in an aqueous polymerization medium, preference is given to keeping the pH in the range from 2 to 10, in particular from 3 to 8, during the polymerization.

Suitable free-radical initiators are in particular peroxo compounds, azo compounds, redox initiator systems and reducing compounds. It will be appreciated that mixtures of free-radical initiators may also be used.

Among the thermally activatable polymerization initiators, preference is given to initiators having a 10 h half-life decomposition temperature in the range from 20 to 180° C., in particular from 50 to 120° C. Examples of preferred thermal initiators are inorganic peroxo compounds such as peroxodisulfates (ammonium and alkali metal sulfates, preferably sodium peroxodisulfate), peroxosulfates, percarbonates and hydrogen peroxide; organic peroxo compounds such as diacetyl peroxide, di-tert-butyl peroxide, diamyl peroxide, dioctanoyl peroxide, didecanoyl peroxide, dilauroyl peroxide, dibenzoyl peroxide, bis(o-toluyl)peroxide, succinyl peroxide, tert-butyl peracetate, tert-butyl permaleate, tert-butyl perisobutyrate, tert-butyl perpivalate, tert-butyl peroctoate, tert-butyl perneodecanoate, tert-butyl perbenzoate, tert-butyl peroxide, tert-butyl hydroperoxide, cumene hydroperoxide, tert-butyl peroxy-2-ethylhexanoate and diisopropyl peroxydicarbamate; azo compounds such as 2,2'-azobisisobutyronitrile, 2,2'-azobis(2-methylbutyronitrile) and azobis(2-aminopropane)dihydrochloride.

These initiators may be used in combination with reducing compounds as initiator/regulator systems. Examples of such reducing compounds include phosphorus compounds such as phosphorous acid, hypophosphites and phosphinates, sulfur compounds such as sodium hydrogensulfite, sodium sulfite and sodium formaldehydesulfoxylate, and also hydrazine. Suitable combinations are, for example, tert-butyl hydroperoxide/sodium disulfite and tert-butyl hydroperoxide/sodium hydroxymethanesulfinate; and also systems with addition of small amounts of redox metal salts such as iron salts, for example ascorbic acid/iron(II) sulfate/sodium peroxodisulfate.

Preferred initiators are soluble in the polymerization medium in the amount used. Preference is therefore given particularly to water-soluble initiators. Particularly preferred initiators are the aforementioned diazo compounds, especially water-soluble diazo compounds such as azobis(2-aminopropane)dihydrochloride.

Likewise suitable are photoinitiators, for example benzophenone, acetophenone, benzoin ether, benzyl dialkyl ketones and derivatives thereof.

Depending on the requirements of the material to be polymerized, the polymerization initiators are used typically in amounts of from 0.01 to 15% by weight, preferably from 0.25 to 5% by weight, based in each case on the monomers to be polymerized, and may be used individually or in combination with one another to utilize advantageous synergistic effects.

To limit the molar masses of the inventive copolymers, customary regulators may be added in the polymerization, for example mercapto compounds such as mercaptoethanol, thioglycolic acid, 1,4-bismercaptobutane-2,3-diol; alkali metal sulfites and hydrogensulfites such as sodium sulfite; alkali metal phosphites and hypophosphites such as sodium hypophosphite, etc. Suitable amounts of regulator are generally in the range from 0.01 to 5% by weight, based on the monomers to be polymerized.

The polymerization temperature is generally in the range from 10 to 200° C., preferably from 40 to 140° C., more preferably from 50 to 120° C.

The polymerization may be carried out under atmospheric pressure; if appropriate, it may also be undertaken in closed systems under the autogenous pressure which develops.

Frequently, the preparation of the copolymers is followed by a chemical and/or physical deodorization, i.e. removal of unconverted monomers. In the physical deodorization, the monomers are removed from the polymerization mixture using water vapor, for example by distilling off a portion of the aqueous polymerization medium and/or by means of passing through steam. In the chemical deodorization, unconverted monomers in the reaction mixture are removed by applying more severe polymerization conditions, for example by adding further polymerization initiator, frequently by adding the abovementioned redox initiators and especially by adding hydroperoxides such as hydrogen peroxide and alkyl hydroperoxides, for example tert-butyl hydroperoxide, in combination with reducing agents, in particular sulfur-containing reducing agents such as hydrogensulfite, dithionite, adducts of hydrogensulfite to ketones such as the acetone-bisulfite adduct, hydroxymethanesulfinate and the like, if appropriate in the presence of traces of transition metals, for example $Fe^{2+}$ or $Fe^{3+}$.

Alternatively to the process described, the inventive copolymers may also be obtained by bonding the poly-$C_2$-$C_4$-alkylene oxide groups Z of the monomer units B to a precursor polymer by polymer-like reaction of suitable functional groups which are present in said precursor copolymer and are bonded to the monomer units $X—CH{=}CR^1—$ of the monomers B. Useful polymer-like reactions include, for example, amidation, transamidation, transesterification or alkoxylation of (meth)acrylic acid units, (meth)acrylic ester units, (meth)acrylamide units and maleic acid units, maleic (mono)ester units, maleic(mono)amide units, vinyl alcohol units, allyl alcohol units, vinylamine units and allylamine units present in the polymer molecule, in particular the polymer-like esterification and amidation of precursor polymers containing (meth)acrylic acid units.

When the inventive copolymers are accordingly to be based on (meth)acrylic esters or (meth)acrylamides as components of monomer units B, the procedure may be, for example, to copolymerize (meth)acrylic acid in an amount equivalent to the molar amount of monomer B with monomer A and also, if appropriate, monomer C, and subsequently to esterify or aminate the copolymer formed with polyalkylene glycols which are not terminally capped, terminally capped at one end by alkyl, phenyl or alkylphenyl radicals, or aminated at one end, or terminally capped at one end by alkyl, phenyl or alkylphenyl radicals and aminated at one end.

When the monomer A used is vinylpyridine N-oxide, it has been found to be advantageous to initially copolymerize the desired amount of the vinylpyridine compound in question with the remaining monomers and subsequently to oxidize the copolymerized vinylpyridine to vinylpyridine N-oxide units.

The inventive copolymers are outstandingly suitable as dye transfer inhibitors in the washing of colored textiles. They reduce or prevent, in an effective manner, dye transfer between the textiles. Moreover, they are universally usable in highly differing detergents such as liquid and solid detergents or detergent formulations. In particular, they have good compatibility with the remaining detergent components, especially with regard to liquid detergents and detergent formulations.

For the purposes of the present invention, good compatibility means that the inventive copolymers can be readily incorporated or formulated into detergent formulations comprising conventional components without the occurrence of demixing operations, and that the resulting detergents or detergent formulations have good stability, especially with respect to demixing, in the course of typical shelf lives. In the case of liquid detergent formulations, this means in particular that there is no significant precipitation of the inventive copolymers and no cloudiness before and during use.

It is assumed that the dye transfer-inhibiting action of the inventive copolymers can be attributed to the N-heterocyclic groups of the monomers A. Accordingly, in view of the good compatibility of the inventive copolymers with customary detergent constituents, it is assumed that said compatibility is attributable to the alkylene oxide units present in the monomers B. This effect is surprising especially because the prior art graft polymers (see, for example, DE 10156134), some of which include similar structural features, have compatibility which is not fully satisfactory.

The inventive copolymers are generally used in amounts in the range from 0.05 to 5% by weight, preferably from 0.1 to 2% by weight, based in each case on the total weight of the detergents or detergent formulations. They are suitable for both heavy duty detergents and for specialty detergents such as color detergents. In dye-protecting color detergents, they are typically used in amounts in the range from 0.1 to 1.5% by weight, preferably from 0.1 to 1% by weight, based in each case on the total weight of the detergents or detergent formulations.

The detergents may be used in solid form, for example in powder, granule, extrudate or tablet form, and also as compact detergents having a bulk density in the range from 500 to 950 g/l, or in a liquid version. They comprise the typically used anionic, nonionic and/or cationic surfactants in amounts of from 2 to 50% by weight, preferably from 8 to 30% by weight, based in each case on the total weight of the detergents or detergent formulations. Particular preference is given to producing phosphate-free or reduced-phosphate detergents which have a phosphate content of at most 25% by weight, based in each case on the total weight of the detergents or detergent formulations, calculated as pentasodium tripolyphosphate.

Suitable anionic surfactants are, for example, $C_8$-$C_{22}$-, preferably $C_{10}$-$C_{18}$-fatty alcohol sulfates, for example $C_9$/$C_{11}$-alcohol sulfate, $C_{12}$/$C_{14}$-alcohol sulfate, lauryl sulfate, cetyl sulfate, myristyl sulfate, palmityl sulfate, stearyl sulfate and tallow fat alcohol sulfate.

Further suitable anionic surfactants are sulfated alkoxylated $C_8$-$C_{22}$-, preferably $C_{10}$-$C_{18}$-alcohols or soluble salts thereof. Compounds of this type are prepared, for example, by initially alkoxylating the alcohol and subsequently sulfating the alkoxylation product. For the alkoxylation, preference is given to using ethylene oxide, in which case from 2 to 50 mol, in particular from 3 to 20 mol, of ethylene oxide are used per mole of fatty alcohol. However, the alkoxylation may also be carried out with propylene oxide or with butylene oxide. It will be appreciated that the alkylene oxides may also be used in combination. The alkoxylated alcohols may in that case contain the ethylene oxide, propylene oxide and/or butylene oxide units in the form of blocks or in random distribution.

Also suitable as anionic surfactants are alkylsulfonates, especially $C_8$-$C_{24}$- and in particular $C_{10}$-$C_{18}$-alkylsulfonates, and also soaps, for example the salts of aliphatic $C_8$-$C_{24}$-carboxylic acids.

Further suitable anionic surfactants are linear $C_9$-$C_{20}$-alkylbenzenesulfonates (LAS).

The anionic surfactants are added to the detergent preferably in the form of salts. Suitable cations are alkali metal ions such as sodium, potassium and lithium ions, and ammonium ions, for example hydroxyethylammonium, di(hydroxyethyl)ammonium and tri(hydroxyethyl)ammonium ions.

Suitable nonionic surfactants are, for example, alkoxylated $C_8$-$C_{22}$-, in particular $C_{10}$-$C_{18}$-alcohols, such as fatty alcohol alkoxylates, oxo alcohol alkoxylates and Guerbet alcohol alkoxylates. The alkoxylation may be carried out using ethylene oxide, propylene oxide and/or butylene oxide. The alkoxylated alcohols may in that case contain the alkylene oxide units in the form of blocks or in random distribution. From 2 to 50 mol, preferably from 3 to 20 mol, of at least one of these alkylene oxides are used per mole of alcohol. The alkylene oxide used is preferably ethylene oxide.

Further suitable nonionic surfactants are alkylphenol alkoxylates, in particular $C_6$-$C_{14}$-alkylphenol ethoxylates having on average from 5 to 30 alkylene oxide units.

Further suitable nonionic surfactants are $C_8$-$C_{22}$-, in particular $C_{10}$-$C_{18}$-alkylpolyglucosides. These compounds contain from 1 to 20, preferably from 1.1 to 5, glucoside units.

A further class of suitable nonionic surfactants is that of N-alkylglucamides of the structures (NT1) and (NT2):

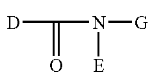

(NT1)

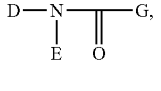

(NT2)

in which D is $C_6$-$C_{22}$-alkyl, preferably $C_{10}$-$C_{18}$-alkyl, E is hydrogen or $C_1$-$C_4$-alkyl, preferably methyl, and G is polyhydroxy-$C_5$-$C_{12}$-alkyl having at least 3 hydroxyl groups, preferably polyhydroxy-$C_5$-$C_6$-alkyl. For example, such compounds are obtained by acylating reducing aminated sugars with acid chlorides of $C_{10}$-$C_{18}$-carboxylic acids.

The detergent formulations preferably comprise $C_{10}$-$C_{18}$-alcohols ethoxylated with from 3 to 12 mol of ethylene oxide as nonionic surfactants.

Particularly suitable cationic surfactants are, for example, $C_7$-$C_{25}$-alkylamines; $C_7$-$C_{25}$-N,N-dimethyl-N-(hydroxyalkyl)ammonium salts; quaternized mono- and di($C_7$-$C_{25}$-)-alkyldimethylammonium compounds; ester quats such as quaternized esterified mono-, di- or trialkanolamines which have been esterified with $C_8$-$C_{22}$-carboxylic acids; and imidazoline quats such as 1-alkylimidazolinium salts of the general formulae KT1 or KT2:

(KT1)

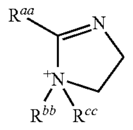

(KT2)

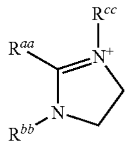

where $R^{aa}$ is $C_1$-$C_{25}$-alkyl or $C_2$-$C_{25}$-alkenyl, $R^{bb}$ is $C_1$-$C_4$-alkyl or -hydroxyalkyl and $R^{cc}$ is $C_1$-$C_4$-alkyl, -hydroxyalkyl or an $R^{aa}$—(CO)—$^2$—$(CH_2)_n$— radical where $W^2$=O or NH and n=2 or 3, and at least one $R^{aa}$ is $C_7$-$C_{22}$-alkyl.

The pulverulent and granular detergents and also, if appropriate, structures (multiphasic) liquid detergents also comprise one or more inorganic builders. Suitable inorganic builders are also customarily used compounds such as aluminosilicates, silicates, carbonates and polyphosphates.

Specific examples include crystalline and amorphous aluminosilicates having ion-exchanging properties, such as zeolites, for example zeolite A, X, B, P, MAP and HS in their sodium form and in forms in which sodium has been partly exchanged for other cations such as Li, K, Ca, Mg or ammonium.

Suitable silicates are, for example, amorphous and crystalline silicates such as amorphous disilicates, sodium metasilicate, crystalline disilicates and sheet silicates, for example the sheet silicate SKS-6 (Clariant AG). The silicates may be used in the form of their alkali metal, alkaline earth metal or ammonium salts. Preference is given to using sodium silicates, lithium silicates and magnesium silicates.

Carbonates and hydrogencarbonates suitable as inorganic builders may likewise be used in the form of their alkali metal, alkaline earth metal and ammonium salts. Preference is given to carbonates and hydrogencarbonates of sodium, lithium and magnesium; particular preference is given to sodium carbonate and/or sodium hydrogencarbonate. An especially suitable phosphate is pentasodium triphosphate.

The inorganic builders may be present in the detergents in amounts of from 5 to 60% by weight. They may be incorporated into the detergent alone or in any combinations with one another. In pulverulent and granular detergents, they are added in amounts of from 10 to 60% by weight, preferably from 20 to 50% by weight. In structured liquid detergents, inorganic builders are used in amounts of up to 40% by weight, preferably up to 20% by weight. In this case, they are suspended in the liquid formulation constituents.

In addition to the inorganic builders, the detergents comprise one or more organic cobuilders.

Suitable organic cobuilders are in particular:

Low molecular weight carboxylic acids such as citric acid, hydrophobically modified citric acid, for example agaric acid, malic acid, tartaric acid, gluconic acid, glutaric acid, succinic acid, imidodisuccinic acid, oxydisuccinic acid, propanetricarboxylic acid, butanetetracarboxylic acid, cyclopentanetetracarboxylic acid, alkyl- and alkenylsuccinic acids and aminopolycarboxylic acids, for example nitrilotriacetic acid, β-alaninediacetic acid, ethylenediaminetetraacetic acid, serinediacetic acid, isoserinediacetic acid, N-(2-hydroxyethyl)iminodiacetic acid, ethylenediaminedisuccinic acid and methyl- and ethylglycinediacetic acid.

Oligomeric and polymeric carboxylic acids such as homopolymers of acrylic acid and aspartic acid, oligomaleic acids, copolymers of maleic acid with acrylic acid, methacrylic acid or $C_2$-$C_{22}$-olefins, for example isobutene or long-chain α-olefins, vinyl $C_1$-$C_8$-alkyl ethers, vinyl acetate, vinyl propionate, (meth)acrylic esters of $C_1$-$C_8$-alcohols and styrene. Preference is given to the homopolymers of acrylic acid and copolymers of acrylic acid with maleic acid. The oligomeric and polymeric carboxylic acids are used in acid form or as the sodium salt.

The organic cobuilders are present in the pulverulent and granular, and also in the structured liquid detergent formulations in amounts of from 0.1 to 15% by weight, preferably from 0.25 to 8% by weight. In liquid detergent formulations, they are present in amounts of from 0.1 to 20% by weight and preferably from 0.25 to 10% by weight.

The pulverulent and granular heavy duty detergents may also comprise a bleach system consisting of at least one bleach, optionally in combination with a bleach activator and/or a bleach catalyst.

Suitable bleaches are, for example, adducts of hydrogen peroxide to inorganic salts, such as sodium perborate monohydrate, sodium perborate tetrahydrate and sodium carbonate perhydrate, and also inorganic and organic peracids in the form of their alkali metal or magnesium salts or in some cases also in the form of the free acids. Examples of suitable organic percarboxylic acids and salts thereof are magnesium monoperphthalate, phthalimidopercaprylic acid and dodecane-1,10-dioic peracid. An example of an inorganic peracid salt is potassium peroxomonosulfate (Oxon).

If bleaches are used, they are present in the formulations in amounts of from 5 to 30% by weight, preferably from 10 to 25% by weight.

Suitable bleach activators are, for example: acylamines such as N,N,N',N'-tetraacetylethylenediamine (TAED), tetraacetylglycoluril, N,N'-diacetyl-N,N'-dimethylurea and 1,5-diacetyl-2,4-dioxohexahydro-1,3,5-triazine; acylated lactams such as acetylcaprolactam, octanoylcaprolactam and benzoylcaprolactam; substituted phenol esters of carboxylic acids such as sodium acetoxybenzenesulfonate, sodium octanoyloxybenzenesulfonate and sodium p-nonanoyloxybenzenesulfonate; N-methylmorpholinium acetonitrilemethylsulfate and hydrogensulfate; acylated sugars such as pentaacetylglucose; anthranil derivatives such as 2-methylanthranil and 2-phenylanthranil; enol esters such as isopropenyl acetate; oxime esters such as o-acetylacetone oxime; carboxylic anhydrides such as phthalic anhydride and acetic anhydride.

Preference is given to using tetraacetylethylenediamine, sodium nonanoyloxybenzenesulfonate and N-methylmorpholinium acetonitrilemethylsulfate and hydrogensulfate as bleach activators.

If the bleach activators are used in detergents, they are present in amounts of from 0.1 to 15% by weight, preferably in amounts of from 1 to 8% by weight, more preferably in amounts of from 1.5 to 6% by weight.

Suitable bleach catalysts are quaternized imines and sulfonimines and manganese and cobalt complexes. If bleach catalysts are used in the detergent formulations, they are present in amounts of up to 1.5% by weight, preferably up to 0.5% by weight; in the case of the very active manganese complexes in amounts of up to 0.1% by weight.

The detergents preferably comprise an enzyme system. This typically comprises proteases, lipases, amylases or cellulases. The enzyme system may be restricted to a single enzyme or include a combination of different enzymes. Of the commercial enzymes, amounts of from 0.1 to 1.5% by weight, preferably from 0.2 to 1% by weight, of the formulated enzymes are generally added to the detergents. Suitable proteases are, for example, Savinase and Esperase (manufacturer Novo Nordisk); a suitable lipase is, for example, Lipolase (manufacturer Novo Nordisk); a suitable cellulase is, for example, Celluzym (manufacturer likewise Novo Nordisk).

The detergents preferably also comprise soil-release polymers and/or graying inhibitors. These are, for example, polyesters composed of polyethylene oxides capped at one end by di- and/or polyhydric alcohols, in particular ethylene glycol and/or propylene glycol (alcohol component), and aromatic dicarboxylic acids or aromatic and aliphatic dicarboxylic acids (acid component).

Further suitable soil-release polymers are amphiphilic graft polymers and copolymers of vinylic and/or acrylic esters, on or with polyalkylene oxides and modified celluloses, for example methylcellulose, hydroxypropylcellulose and carboxymethylcellulose.

Soil-release polymers used with preference are graft polymers of vinyl acetate on polyethylene oxide of average molecular weight $M_w$ from 2500 to 8000 in a weight ratio of from 1.2:1 to 3:1, and also commercial polyethylene terephthalate/polyoxyethylene terephthalates of average molecular weight $M_w$ from 3000 to 25 000, composed of polyethylene oxides of average molecular weight $M_w$ from 750 to 5000 with terephthalic acid and ethylene oxide and a molar ratio of polyethylene terephthalate to polyoxyethylene terephthalate of from 8:1 to 1:1 and block polycondensates which contain blocks of (a) ester units of polyalkylene glycols of average molecular weight $M_w$ from 500 to 7500 and aliphatic dicarboxylic acids and/or monohydroxy monocarboxylic acids, and (b) ester units of aromatic dicarboxylic acids and polyhydric alcohols. These amphiphilic block polymers have average molecular weights $M_w$ of from 1500 to 25 000.

Graying inhibitors and soil-release polymers are present in the detergent formulations in amounts of from 0 to 2.5% by weight, preferably from 0.2 to 1.5% by weight, more preferably from 0.3 to 1.2% by weight.

The invention further provides a solid detergent formulation comprising a) from 0.05 to 5% by weight, preferably from 0.1 to 2% by weight, of the inventive dye transfer-inhibiting copolymer;
b) from 0.5 to 40% by weight of at least one nonionic, anionic and/or cationic surfactant;
c) from 0.5 to 50% by weight of at least one inorganic builder;
d) from 0 to 10% by weight of at least one organic cobuilder;
e) from 0 to 60% by weight of other customary ingredients such as extenders, enzymes, perfume, complexing agents, corrosion inhibitors, bleaches, bleach activators, bleach catalysts, further dye transfer inhibitors, graying inhibitors, soil-release polyesters, fiber and color protection additives, silicones, dyes, bactericides, dissolution improvers and/or disintegrants;

the sum of the components a) to e) being 100% by weight.

The invention further provides a liquid detergent formulation comprising a) from 0.05 to 5% by weight, preferably from 0.1 to 2% by weight, of the inventive dye transfer-inhibiting copolymer;
b) from 0.5 to 40% by weight of at least one nonionic, anionic and/or cationic surfactant;
c) from 0 to 20% by weight of at least one inorganic builder;
d) from 0 to 10% by weight of at least one organic cobuilder;
e) from 0 to 60% by weight of other customary ingredients such as sodium carbonate, enzymes, perfume, complexing agents, corrosion inhibitors, bleaches, bleach activators, bleach catalysts, further dye transfer inhibitors, graying inhibitors, soil-release polyesters, fiber and color protection additives, silicones, dyes, bactericides, solubilizers, hydrotropes, thickeners and/or alkanolamines; and
f) from 0 to 99.45% by weight of water, and/or polyhydric, water-miscible alcohols, such as monopropylene glycol, dipropylene glycol and glycerol, and also mixtures thereof.

A detailed description of the detergent ingredients can be found, for example, in WO 99/06524 or WO 99/04313, and in Liquid Detergents, Editor: Kuo-Yann Lai, Surfactant Sci. Ser.; Vol. 67, Marcel Dekker, New York, 1997, p. 272-304.

In addition, the inventive copolymers are suitable for the following applications: as brighteners in cleaning compositions, assistants in textile production, assistants in cosmetic formulations, adjuvants in agrochemical formulations, additives in water treatment, assistants in metal processing agents and cooling lubricants, and also as gas hydrate inhibitors and in other fields of application in the oilfield sector.

The examples which follow serve to illustrate the invention.

POLYMERIZATION EXAMPLES

Example 1

In a reactor, 800 g of distilled water were heated to an internal temperature of approx. 82° C. (T) with supply of nitrogen. Then, 360 g of vinylpyrrolidone (VP) and, in parallel, a mixture of 20.8 g of methacrylic acid (MAS), 19.2 g of α-methoxy ω-methacryloyl polyethylene glycol (having a number-average molecular weight of the polyethylene glycol (PEG) of approx. 1000) (MPEGMA) and 60 g of water (W1) were metered in continuously (i.e. at constant rate) within 3 h. At the same time, 8 g of 2,2'-azobis(2-methylpropionamidine)dihydrochloride (V-50, Wako Chemicals) (V50) in 80 g of water (W2) were metered in continuously within 4 h. Then, the mixture was stirred under a nitrogen atmosphere at 82° C. for a further hour. Within 30 min, 2 g of 2,2'-azobis(2-methylpropionamidine)dihydrochloride in 20 g of water were added. After stirring at 82° C. for a further 2 h, the solution was adjusted to a pH of 7.2 using 50% aqueous sodium hydroxide solution. A slightly yellowish, clear solution having a solids content (S.C.) of 28% and a K value (1% by weight in aqueous solution) of 28.0 was obtained.

Examples 2 to 10 were carried out in a similar manner to Example 1, except that in each case the amounts, specified below in Table 1, of vinylpyrrolidone (VP), if appropriate as a mixture with the amount of vinylimidazole (VI) specified in each case, and also of methacrylic acid (MAA), α-methoxy ω-methacryloyl polyethylene glycol (MPEGMA), water (W1 and W2) and 2,2'-azobis(2-methylpropionamidine)dihydrochloride (V50) were used.

TABLE 1

| Example | T [° C.] | VP [g] | VP [mol %] | VI [g] | VI [mol %] | MAA [g] | MAA [mol %] | MPEGMA [g] | MPEGMA [mol %] | W1 [g] | V50 [g] | W2 [g] | K value | S.C. [%] |
|---|---|---|---|---|---|---|---|---|---|---|---|---|---|---|
| 1 | 82 | 360 | 92.6 | — | — | 20.8 | 6.92 | 19.2 | 0.5 | 60 | 8 | 80 | 28 | 28 |
| 2 | 82 | 360 | 98.9 | — | — | — | — | 40 | 1.1 | 40 | 8 | 80 | 35.4 | 30.4 |
| 3 | 85 | 280 | 95.9 | — | — | — | — | 120 | 4.1 | 120 | 8 | 80 | 35.9 | 28.3 |
| 4 | 96 | 320 | 97.6 | — | — | — | — | 80 | 2.4 | 80 | 12 | 120 | 31.5 | 28.6 |
| 5 | 95 | 360 | 98.6 | — | — | — | — | 20* | 1.3 | 20 | 12 | 120 | 31.4 | 29.8 |
| 6 | 95 | 320 | 94.2 | — | — | — | — | 80* | 5.8 | 80 | 12 | 120 | 33.3 | 28.9 |
| 7 | 95 | 360 | 98.1 | — | — | — | — | 40⁺ | 1.9 | 40 | 12 | 120 | 28.8 | 27.3 |
| 8 | 95 | 320 | 97.9 | — | — | — | — | 40⁺ | 2.1 | 40 | 12 | 120 | 30.3 | 27 |
| 9 | 97 | 160 | 39.4 | 160 | 46.5 | 41.6 | 13.1 | 38.4 | 1.0 | 80 | 16 | 160 | 32.4 | 29.2 |
| 10 | 97 | 160 | 44.8 | 160 | 52.9 | — | — | 80 | 2.3 | 80 | 16 | 160 | 34.4 | 28.3 |

*The $M_n$ value of the MPEGMA is 350 g/mol
⁺The $M_n$ value of the MPEGMA is 550 g/mol

Examples 11 to 20

Example 11

In a reactor, 385 g of distilled water and 80 g of allyl ether ethoxylate (allyl alcohol with 10 ethylene oxide (EO) units) were heated to an internal temperature of 87° C. (T) with supply of nitrogen. Then, 320 g of vinylpyrrolidone (VP) were metered in continuously within 3 h. Approx. 5 minutes later, a solution of 6.4 g of 2,2'-azobis(2-methylpropionamidine)dihydrochloride (V50) in 58 g of water was metered in continuously within 3 h. Then, the mixture was stirred under a nitrogen atmosphere at 87° C. for a further hour. The mixture was subsequently cooled to an internal temperature of 60° C., then 2.3 g of tert-butyl hydroperoxide (70%) dissolved in 14 g of water (W3) were added all at once. Subsequently, 1.6 g of sodium disulfite dissolved in 50 g of deionized water were added within 30 minutes. The mixture was stirred at 60° C. for yet a further hour. A slightly yellowish, clear solution having a solids content of 46.2% and a K value (1% by weight in 3% by weight aqueous NaCl solution) of 33.7 was obtained.

Examples 13, 15 and 16 were carried out in a similar manner to Example 11.

Example 12

In a reactor, 385 g of dist. water and 80 g of allyl ether ethoxylate (allyl alcohol with 10 EO units) were heated to an internal temperature of 87° C. with supply of nitrogen. Then, 320 g of vinylpyrrolidone (VP) were metered in continuously within 2 h. Approx. 5 minutes later, a solution of 6.4 g of 2,2'-azobis(2-methylpropionamidine)dihydrochloride (V50) in 58 g of water was metered in continuously within 2 h. The mixture was then stirred under a nitrogen atmosphere at 87° C. for a further hour. The mixture was subsequently cooled to an internal temperature of 60° C.; then 2.3 g of tert-butyl hydroperoxide (70%) dissolved in 14 g of water were added all at once. Subsequently, 1.6 g of sodium disulfite dissolved in 50 g of deionized water were added within 30 minutes. The mixture was stirred at 60° C. for yet a further hour. A slightly yellowish, clear solution having a solids content of 46.7% and a K value (1% by weight in 3% by weight NaCl solution) of 36.7 was obtained.

Examples 14 and 17 were carried out in a similar manner to Example 12.

Example 18

In a reactor, 385 g of distilled water and 80 g of allyl ether ethoxylate (allyl alcohol with 16.6 EO units) were heated to an internal temperature of 87° C. (T) with supply of nitrogen. Then, 220 g of vinylpyrrolidone (VP) and 100 g of vinylimidazole (VI) were simultaneously metered in continuously within 3 h. Approx. 5 minutes later, a solution of 6.4 g of 2,2'-azobis(2-methylpropionamidine)dihydrochloride (V50) in 58 g of water was metered in continuously within 3 h. Then, the mixture was stirred under a nitrogen atmosphere at 87° C. for a further hour. A slightly yellowish, clear solution having a solids content of 48.7% and a K value (1% by weight in 3% by weight aqueous NaCl solution) of 41.5 was obtained.

Example 19 was carried out in a similar manner to Example 18.

Example 20

In a reactor, 385 g of dist. water and 80 g of allyl ether ethoxylate (allyl alcohol with 16.6 EO units) were heated to an internal temperature of 87° C. (T) with supply of nitrogen. Then, 220 g of vinylpyrrolidone (VP) and 100 g of vinylimidazole (VI) were simultaneously metered in continuously within 3 h. Approx. 5 minutes later, a solution of 6.4 g of 2,2'-azobis(2-methylpropionamidine)dihydrochloride (V50) in 58 g of water and also a further solution of 1.2 g of mercaptoethanol (ME) dissolved in 11 g of water were metered in continuously within 3 h. Then, the mixture was stirred under a nitrogen atmosphere at 87° C. for a further hour. Subsequently, the mixture was cooled to an internal temperature of 60° C., then 2.3 g of tert-butyl hydroperoxide (70%) dissolved in 14 g of water were added all at once. Subsequently, 1.6 g of sodium disulfite dissolved in 50 g of deionized water were added within 30 minutes. The mixture was then stirred at 60° C. for yet a further hour. A slightly yellowish, clear solution having a solids content of 45.8% and a K value (1% by weight in 3% by weight aqueous NaCl solution) of 34.4 was obtained.

Example 21 was carried out in a similar manner to Example 20.

Example 23

In a reactor, 385 g of distilled water and 80 g of allyl ether ethoxylate (allyl alcohol with 16.6 EO units) were heated to an internal temperature of 87° C. with supply of nitrogen. Then, 320 g of vinylpyrrolidone (VP) were simultaneously metered in continuously within 3 h. Approx. 5 minutes later, a solution of 6.4 g of 2,2'-azobis(2-methylpropionamidine) dihydrochloride (V50) in 58 g of water and also a further solution of 1.6 g of mercaptoethanol (ME) dissolved in 14.4 g of water were metered in continuously within 3 h. Then, the mixture was stirred under a nitrogen atmosphere at 87° C. for a further hour. Subsequently, the mixture was cooled to an internal temperature of 60° C., then 2.3 g of tert-butyl hydroperoxide (70%) dissolved in 14 g of water were added all at once. Subsequently, 1.6 g of sodium disulfite dissolved in 50 g of deionized water were added within 30 minutes. The mixture was then stirred at 60° C. for yet a further hour. A slightly yellowish, clear solution having a solids content of 32% and a K value (1% by weight in 3% by weight aqueous NaCl solution) of 31 was obtained.

Example 22 was carried out in a similar manner to Example 23, except that no mercaptoethanol (ME) was metered in.

Example 24

In a reactor, 385 g of distilled water and 80 g of allyl ether ethoxylate (allyl alcohol with 1 EO and 42 propylene oxide (PO) units) were heated to an internal temperature of 87° C. with supply of nitrogen. Then, 160 g of vinylpyrrolidone (VP) and 160 g of vinylimidazole (VI) were simultaneously metered in continuously within 3 h. Approx. 5 minutes later, a solution of 6.4 g of 2,2'-azobis(2-methylpropionamidine) dihydrochloride (V50) in 50 g of water was metered in continuously within 3 h. Then, the mixture was stirred under a nitrogen atmosphere at 87° C. for a further hour. Subsequently, the mixture was cooled to an internal temperature of 60° C., then 2.3 g of tert-butyl hydroperoxide (70%) dissolved in 14 g of water were added all at once. Subsequently, 1.6 g of sodium disulfite dissolved in 50 g of deionized water were added within 30 minutes. The mixture was then stirred at 60° C. for yet a further hour. A slightly yellowish, clear solution having a solids content of 39.8% and a K value (1% by weight in 3% by weight aqueous NaCl solution) of 40.5 was obtained.

Example 25

In a reactor, 385 g of distilled water and 80 g of allyl ether ethoxylate (allyl alcohol with 1 EO and 42 propylene oxide (PO) units) were heated to an internal temperature of 87° C. (T) with supply of nitrogen. Then, 160 g of vinylpyrrolidone (VP) and, in parallel, 160 g of vinylimidazole (VI) were simultaneously metered in continuously within 3 h. Approx. 5 minutes later, one solution each of 6.4 g of 2,2'-azobis(2-methylpropionamidine)dihydrochloride (V50) in 50 g of water and of 1.2 g of mercaptoethanol (ME) in 11 g of distilled water were metered in continuously within 3 h. Then, the mixture was stirred under a nitrogen atmosphere at 87° C. for a further hour. A slightly yellowish, clear solution having a solids content of 38.4% and a K value (1% by weight in 3% by weight aqueous NaCl solution) of 31.8 was obtained.

The Tables 2a and 2b which follow summarize the parameters of the experimental procedures of Examples 11 to 25.

TABLE 2a

| Example | VP [g] | VP [mol %] | VI [g] | VI [mol %] | Allyl alcohol ethoxylate [g]/[number of EO units]/[mol %] | V50 [g] | K value | S.C. [%] |
|---|---|---|---|---|---|---|---|---|
| 11 | 320 | 94.7 | — | — | 80/10/5.3 | 6.4 | 33.7 | 46.2 |
| 12 | 320 | 94.7 | — | — | 80/10/5.3 | 4.0 | 36.7 | 46.7 |
| 13 | 320 | 94.7 | — | — | 80/10/5.3 | 4.0 | 32.8 | 46.9 |
| 14 | 320 | 94.7 | — | — | 80/10/5.3 | 4.0 | 31.5 | 45.9 |
| 15 | 340 | 96.3 | — | — | 60/10/3.8 | 6.4 | 32.6 | 52.3 |
| 16 | 340 | 96.3 | — | — | 60/10/3.8 | 4.0 | 35 | 53.2 |
| 17 | 340 | 96.3 | — | — | 60/10/3.8 | 4.0 | 39.6 | 52.3 |
| 18 | 220 | 63.0 | 100 | 33.8 | 80/16.6/3.2 | 6.4 | 41.5 | 48.7 |
| 19 | 160 | 44.4 | 160 | 52.5 | 80/16.6/3.1 | 6.4 | 43.3 | 48.9 |

TABLE 2b

| Example | VP [g] | VP [mol %] | VI [g] | VI [mol %] | Allyl alcohol ethoxylate [g]/EO fraction#/ PO fraction#/ [mol %] | V50 [g] | ME [g] | K value | S.C. [%] |
|---|---|---|---|---|---|---|---|---|---|
| 20 | 220 | 63.0 | 100 | 33.8 | 80/16.6/—/3.2 | 6.4 | 1.2 | 34.4 | 45.8 |
| 21 | 160 | 44.4 | 160 | 52.5 | 80/16.6/—/3.1 | 6.4 | 1.6 | 32.7 | 45.1 |
| 22 | 320 | 94.7 | — | — | 80/10/—/5.3 | 6.4 | — | 35.4 | 28 |
| 23 | 320 | 96.6 | — | — | 80/16.6/—/3.4 | 6.4 | 1.6 | 31 | 32 |
| 24 | 160 | 45.4 | 160 | 53.6 | 80/1/42/1.0 | 6.4 | — | 40.5 | 39.8 |
| 25 | 160 | 45.4 | 160 | 53.6 | 80/1/42/1.0 | 6.4 | 1.2 | 31.8 | 38.4 |

#Number of EO and PO units (number average)

APPLICATION EXAMPLES

Testing of Inventive copolymers as Dye Transfer Inhibitors in Detergents

The invention copolymers were tested as dye transfer inhibitors in detergents. For this purpose, two granular detergents (DE1, DE2) and two liquid detergents (DE3, DE4) of the compositions listed in Table 3 were produced by way of example, and DE1 differs from DE2, and DE3 from DE4, each by the content of inventive copolymer (DE1=0.15% by weight; DE2=0.25% by weight; DE3=0.15% by weight; DE4=1% by weight). Then, white cotton test fabric was washed under the wash conditions specified in Table 4 in the presence of dye which was added to the wash liquor as a 0.03 or 0.06% by weight aqueous solution.

The measurement of the dyeing of the test fabric was photometric using the Elrepho 2000 photometer (Datacolor). The reflectance (in %) was measured at the wavelength of the particular maximum absorption of the different dyes. The whiteness of the test fabric after the wash served to assess the dyeing. The measurements reported in Tables 5 a-c were confirmed by multiple repetition and averaging.

Tables 5 a-c list the results of the wash experiments within inventive copolymers in comparison to wash experiments without dye transfer inhibitors.

TABLE 3

Compositions of detergents DE1 to DE4 (data in % by weight)

| | DE1 [%] | DE2 [%] | DE3 [%] | DE4 [%] |
|---|---|---|---|---|
| $C_{12}/C_{14}$ Fatty alcohol sulfate | | | 24 | 24 |
| $C_{12}/C_{14}$ Fatty alcohol ethoxylate | | | 2 | 2 |
| $C_{12}/C_{14}$ Alkylbenzenesulfonate | 9 | 9 | | |
| $C_{13}/C_{15}$ Tallow fat alcohol reacted with 7 EO units | 6.6 | 6.6 | 6 | 6 |
| Coconut fatty acid | | | 5 | 5 |
| Soap | 1.8 | 1.8 | 0.7 | 0.7 |
| Borax | | | 2.2 | 2.2 |
| Zeolite A | 45 | 45 | | |
| Polycarboxylate (acrylic acid/maleic acid copolymer; w/w 70:30, $M_w$ 70000) | 5 | 5 | | |
| Sodium carbonate | 7 | 7 | | |
| Trisodium citrate•2 $H_2O$ | 12 | 12 | 2.1 | 2.1 |
| Magnesium silicate | 0.8 | 0.8 | | |
| Carboxymethylcellulose | 0.8 | 0.8 | | |
| Propylene glycol monomethyl ether | | | 10 | 10 |
| Copolymer (calc. 100%) | 0.15 | 0.25 | 0.15 | 1 |
| Water | ad 100 | ad 100 | ad 100 | ad 100 |

TABLE 4

Wash conditions

| | DE1 | DE2 |
|---|---|---|
| Machine | Launder-o-meter | Launder-o-meter |
| Cycles | 1 | 1 |
| Time | 30 min | 30 min |
| Water hardnesses | 3.0 mmol $Ca^{2+}$/I, molar Ca:Mg:$HCO_3$ ratio: 4:1:8 | 3.0 mmol $Ca^{2+}$/I, molar Ca:Mg:$HCO_3$ ratio: 4:1:8 |
| Temperature | 60° C. | 60° C. |
| Dye introduction | Dye solution | Dye solution |
| Test fabric | Cotton cloth | Cotton cloth |
| Liquor amount | 250 ml | 250 ml |
| Liquor ratio | 1:12.5 | 1:12.5 |
| Detergent concentration | 4.5 g/l | 6 g/l |

TABLE 5a

DE1 wash results

| Copolymer from Ex. | % reflectance Direct Blue 71 | % reflectance Direct Red 212 | % reflectance Direct Black 22 |
|---|---|---|---|
| 1 | 69.5 | 56.1 | 64.6 |
| 2 | 70.2 | 57.3 | 62.6 |
| 3 | 68.9 | 55.7 | 64.8 |
| 4 | 69.2 | 56.1 | 64.4 |
| 5 | 70.1 | 56.6 | 65.5 |
| 6 | 68.5 | 56.0 | 66.5 |
| 7 | 70.0 | 57.4 | 67.3 |
| 8 | 68.8 | 56.6 | 68.1 |
| 9 | 72.5 | 60.4 | 67.0 |
| 10 | 74.7 | 64.6 | 70.3 |
| None | 63.4 | 54.3 | 59.7 |
| Whiteness before the wash | 79.8 | 78.8 | 80 |

TABLE 5b

DE2 Wash results

| Copolymer from Ex. | % reflectance Direct Blue 71 | % reflectance Direct Red 212 | % reflectance Direct Black 22 |
|---|---|---|---|
| 11 | 71.48 | 58.14 | 67.71 |
| 12 | 73.07 | 58.34 | 69.11 |
| 13 | 72.89 | 58.83 | 68.31 |
| 18 | 76.27 | 65.46 | 74.69 |
| 19 | 76.58 | 68.31 | 76.44 |
| 20 | 76.50 | 65.57 | 75.00 |
| 21 | 76.70 | 68.26 | 76.94 |
| 22 | 73.07 | 58.34 | 69.11 |
| 23 | 72.89 | 58.83 | 68.31 |
| 24 | 76.83 | 69.27 | 76.83 |
| 25 | 76.68 | 68.98 | 77.23 |
| None | 63.6 | 53.98 | 65.54 |
| Whiteness before the wash | 79.8 | 78.8 | 80 |

TABLE 5c

DE3 wash results:

| Copolymer from Ex. | % reflectance Direct Blue 71 | % reflectance Direct Red 212 | % reflectance Direct Black 22 |
|---|---|---|---|
| 1 | 69.8 | 57.0 | 70.5 |
| 2 | 69.8 | 56.9 | 70.1 |
| 3 | 69.0 | 57.0 | 70.0 |
| 4 | 68.2 | 56.4 | 69.8 |
| 5 | 69.4 | 55.7 | 69.1 |
| 6 | 67.6 | 55.8 | 69.9 |
| 7 | 69.1 | 56.3 | 69.7 |
| 8 | 68.1 | 55.9 | 70.5 |
| None | 64.5 | 53.7 | 69.8 |
| Whiteness before the wash | 79.8 | 78.8 | 80 |

The wash results obtained demonstrate the very good effectiveness of the inventive copolymers as dye transfer inhibitors, which is independent of the type of the dye.

Testing for Compatibility in Liquid Detergents

To assess the stability of the copolymers in different liquid detergent formulations, in each case 1% by weight of copolymer was formulated into the liquid detergent and a visual assessment with regard to phase separation, cloudiness, incompatibilities, etc. was undertaken.

The stability tests were carried out using liquid detergent formulation DE4.

In Table 6, the visual assessments after storage at 40° C. for 4 weeks are compiled.

TABLE 6

| Copolymer Example No. | DE4 |
|---|---|
| None | Clear |
| Copolymer 1 | Clear |
| Copolymer 3 | Clear |
| Copolymer 9 | Clear |
| Copolymer 10 | Clear |
| Copolymer 11 | Clear |
| Copolymer 22 | Clear |
| Copolymer 23 | Clear |

What is claimed is:

1. A method of reducing or preventing dye transfer between textiles during washing of colored textiles, the method comprising washing the colored textiles in the presence of a solid or liquid detergent comprising a copolymer comprising, in polymerized form, (a) from 80 to 99.9 mol %, based on the total amount of the monomers polymerized to prepare the copolymer, of at least one monomer A which in each case comprises a heterocycle having at least 1 nitrogen atom and composed of from 3 to 10 ring members and a $C_2$-$C_6$-alkenyl group bonded to a carbon or nitrogen ring atom of the heterocycle; and (b) from 0.1 to 20 mol %, based on the total amount of the monomers polymerized to prepare the copolymer, of at least one monomer B copolymerizable with monomer A, said monomer B having a monoethylenically unsaturated double bond and also a linear or branched poly-$C_2$-$C_4$-alkylene oxide group having on average from 4 to 500 $C_2$-$C_4$-alkylene oxide units.

2. The method of claim 1, wherein monomer A comprises at least one N-vinyllactam and, if appropriate, at least one N-vinylimidazole, and both the former and the latter may each have 1, 2, 3 or 4 substituents each independently selected from $C_1$-$C_4$-alkyl, $C_3$-$C_6$-cycloalkyl and phenyl.

3. The method of claim 2, wherein monomer A is selected from N-vinylpyrrolidone and mixtures of N-vinylpyrrolidone with N-vinylimidazole.

4. The method of claim 1, wherein the proportion of ethylene oxide units in monomer B is at least 50% based on the $C_2$-$C_4$-alkylene oxide units present in monomer B.

5. The method of claim 1, wherein the poly-$C_2$-$C_4$-alkylene oxide group in monomer B has 1 or 2 end groups which are each independently selected from H, $C_1$-$C_{10}$-alkyl and benzyl.

6. The method of claim 5, wherein the end groups are selected from $C_1$-$C_2$-alkyl.

7. The method of claim 1, wherein monomer B has the general formula I:

$$X—CH═CR^1—Y—Z \quad (I)$$

where

X is H or COOH;

$R^1$ is H or methyl;

Y is O, $CH_2$—O, C(O)O, C(O)NH, NHC(O) or $CH_2$—NHC(O); and

Z is a linear or branched poly-$C_2$-$C_4$-alkylene oxide group comprising on average from 4 to 500 $C_2$-$C_4$-alkylene oxide units and 1 or 2 terminal radicals each independently selected from H, $C_1$-$C_{10}$-alkyl and benzyl.

8. The method of claim 7, wherein, in formula I, the variable X is H and Y is C(O)O or C(O)NH.

9. The method of claim 8, wherein the terminal radical(s) in Z is/are $C_1$-$C_2$-alkyl.

10. The method of claim 1, wherein monomer B is selected from the methyl polyethylene glycol esters of (meth)acrylic acid and allyl ether ethoxylates.

11. The method of claim 7, wherein, in formula I, the variable X is H and Y is $CH_2$—O.

12. The method of claim 1, wherein the copolymer additionally comprises, in polymerized form, from 1 to 20 mol % of at least one monomer C copolymerizable with monomers A and B, said monomer C being selected from monoethylenically unsaturated $C_3$-$C_{10}$-mono- and -dicarboxylic acids, vinyl esters of saturated $C_1$-$C_{10}$-carboxylic acids, vinyl and allyl ethers of $C_1$-$C_{10}$-alcohols, vinylformamides, quaternary products of N-vinyl- and N-allylamines, and mixtures thereof.

13. The method of claim 12, wherein the proportion of monomer C is at most 20 mol %.

14. The method of claim 1, wherein the copolymer has a K value in the range from 10 to 150.

* * * * *